(12) United States Patent
Swisher

(10) Patent No.: US 7,998,113 B2
(45) Date of Patent: Aug. 16, 2011

(54) MEDICAL DEVICE HAVING PREFILLED BALLOON

(75) Inventor: David Rork Swisher, St. Charles, MO (US)

(73) Assignee: Tyco Healthcare Group LP, Mansfield, MA (US)

( * ) Notice: Subject to any disclaimer, the term of this patent is extended or adjusted under 35 U.S.C. 154(b) by 42 days.

(21) Appl. No.: 12/545,434

(22) Filed: Aug. 21, 2009

(65) Prior Publication Data

US 2010/0081990 A1    Apr. 1, 2010

Related U.S. Application Data

(60) Provisional application No. 61/101,372, filed on Sep. 30, 2008.

(51) Int. Cl.
*A61M 29/00* (2006.01)
(52) U.S. Cl. .................................. 604/101.05
(58) Field of Classification Search ............ 604/101.01, 604/101.05, 104, 107, 174
See application file for complete search history.

(56) References Cited

U.S. PATENT DOCUMENTS

| | | | | |
|---|---|---|---|---|
| 3,190,291 | A * | 6/1965 | Foley | 604/98.01 |
| 3,275,001 | A * | 9/1966 | Rosecrans | 604/98.01 |
| 3,599,620 | A * | 8/1971 | Balin | 604/98.01 |
| 3,602,226 | A * | 8/1971 | Ericson | 604/98.01 |
| 3,675,658 | A * | 7/1972 | Taylor | 604/98.01 |
| 4,909,785 | A | 3/1990 | Burton et al. | |
| 5,188,595 | A | 2/1993 | Jacobi | |
| 5,314,409 | A | 5/1994 | Sarosiek et al. | |
| 5,439,444 | A | 8/1995 | Andersen et al. | |
| 5,445,615 | A | 8/1995 | Yoon | |
| 5,697,946 | A | 12/1997 | Hopper et al. | |
| 5,741,235 | A | 4/1998 | Knight | |
| 5,857,999 | A | 1/1999 | Quick et al. | |
| 6,059,816 | A | 5/2000 | Moenning | |
| 6,077,243 | A | 6/2000 | Quinn | |
| 6,454,785 | B2 | 9/2002 | De Hoyos Garza | |
| 6,802,825 | B2 * | 10/2004 | Ackerman et al. | 604/174 |
| 6,837,871 | B2 | 1/2005 | Gonzales et al. | |
| 6,979,313 | B1 * | 12/2005 | Meek et al. | 604/98.01 |
| 2006/0079838 | A1 | 4/2006 | Walker et al. | |
| 2006/0253099 | A1 * | 11/2006 | Noone | 604/509 |
| 2008/0249504 | A1 | 10/2008 | Lattouf et al. | |

FOREIGN PATENT DOCUMENTS

WO    03094994 A2    11/2003

OTHER PUBLICATIONS

European Search Report regarding related application serial No. EP 09170346.2 dated Dec. 28, 2010, 6 pgs.

* cited by examiner

*Primary Examiner* — Nicholas D Lucchesi
*Assistant Examiner* — Aarti B Berdichevsky

(57) ABSTRACT

A medical device including an element defining a central lumen and a secondary lumen. The device includes a prefilled balloon having an interior surface operatively communicates with the secondary lumen. The device includes a securement balloon having an interior surface communicating with the secondary lumen. The securement balloon, secondary lumen, and prefilled balloon define a closed fluid system. The securement balloon is stronger than the prefilled balloon so fluid in the closed fluid system inflates the prefilled balloon before inflating the securement balloon. The device includes a transfer sleeve movable from a first position spaced from the prefilled balloon to a second position positioned around the prefilled balloon to urge fluid from the prefilled balloon into the securement balloon. When the transfer sleeve is in the first position, the securement balloon is substantially collapsed. When the transfer sleeve is in the second position, the securement balloon is inflated.

20 Claims, 7 Drawing Sheets

MEDICAL DEVICE HAVING PREFILLED BALLOON

CROSS-REFERENCE TO RELATED APPLICATION

The present application is a non-provisional of U.S. patent application Ser. No. 61/101,372, filed Sep. 30, 2008, entitled, "Medical Device with Prefilled Balloon", which is hereby incorporated by reference in its entirety.

FIELD OF THE INVENTION

The present invention generally relates to medical devices that are secured within the body and, more particularly, to a medical device having a prefilled balloon.

BACKGROUND

Medical devices including a balloon that can be expanded to secure one end of the medical device within the body are known in the art. Such devices include urinary catheters, gastrostomy tubes and a variety of other indwelling catheters. Typically, these devices include a catheter having an expandable balloon secured to the distal end of the catheter. The distal end of the catheter is inserted through a body orifice, a stoma, or a small incision into a body organ or body cavity. Next, fluid is injected through a passage in the medical device using, for example, a syringe to inflate the balloon to prevent removal of the distal end of the medical device from the organ or cavity.

One problem associated with medical devices having a securement balloon is that the balloon is the weakest part of the device and over time is susceptible to breakage. Although the safe, useful life of a securement balloon can be easily determined via laboratory testing under prescribed operating conditions, the safe, useful life of a securement balloon is very difficult to determine where clinicians fail to deliver the prescribed amount fluid to inflate the balloon. For example, overfilling a balloon reduces the operating life of the balloon.

Accordingly, a continuing need exists in the medical arts for a medical device having a securement balloon allowing a clinician to repeatedly and accurately fill a balloon with the prescribed amount of fluid.

SUMMARY

In one aspect of the present invention, a medical device comprises an element having a proximal hub portion and a tubular portion extending distally from the hub portion. The element defines a central lumen extending through the hub portion and the tubular portion. The element also defines a secondary lumen having a first open end and a second open end proximal to the first open end. The device further comprises a prefilled balloon positioned around the element such that an interior surface of the prefilled balloon operatively communicates with the second open end of the secondary lumen. The device also comprises securement balloon positioned around the tubular portion distal to the prefilled balloon such that an interior surface of the securement balloon operatively communicates with the first open end of the secondary lumen. The securement balloon, the secondary lumen, and the prefilled balloon define a closed fluid system. The securement balloon is stronger than the prefilled balloon such that fluid in the closed fluid system inflates the prefilled balloon before inflating the securement balloon. The device further comprises a transfer sleeve slidably positioned around the tubular portion. The transfer sleeve is movable along the tubular portion from a first position spaced from the prefilled balloon to a second position positioned around the prefilled balloon to urge fluid from the prefilled balloon into the securement balloon to inflate the securement balloon. When the transfer sleeve is in the first position, the medical device is in a first condition in which the securement balloon is substantially collapsed. When the transfer sleeve is in the second position the medical device is in a second condition in which the securement balloon is inflated.

In another aspect of the present invention, a medical device comprises an element having a proximal hub portion and a tubular portion extending distally from the hub portion. The element defines a central lumen extending through the hub portion and the tubular portion. The element also defines a secondary lumen having a first open end adjacent a distal end of the element and a second open end adjacent a proximal end of the element. The device further comprises a prefilled balloon positioned around the proximal end of the element such that an interior surface of the prefilled balloon communicates with the second open end of the secondary lumen. The device also comprises a securement balloon positioned about the distal end of the tubular portion such that an interior surface of the securement balloon communicates with the first open end of the secondary lumen. The securement balloon, the secondary lumen, and the prefilled balloon define a closed fluid system. The securement balloon is stronger than the prefilled balloon such that fluid in the closed fluid system inflates the prefilled balloon before inflating of the securement balloon. In addition, the device includes a transfer sleeve positionable around the prefilled balloon to urge fluid from the prefilled balloon into the securement balloon to inflate the securement balloon.

Other objects and features will be in part apparent and in part pointed out hereinafter.

BRIEF DESCRIPTION OF THE DRAWINGS

Various embodiments of the presently disclosed medical device having a prefilled balloon ("medical device") are disclosed herein with reference to the drawings, wherein.

Corresponding reference characters indicate corresponding parts throughout the drawings.

DESCRIPTION OF THE EMBODIMENTS

Figure 1:
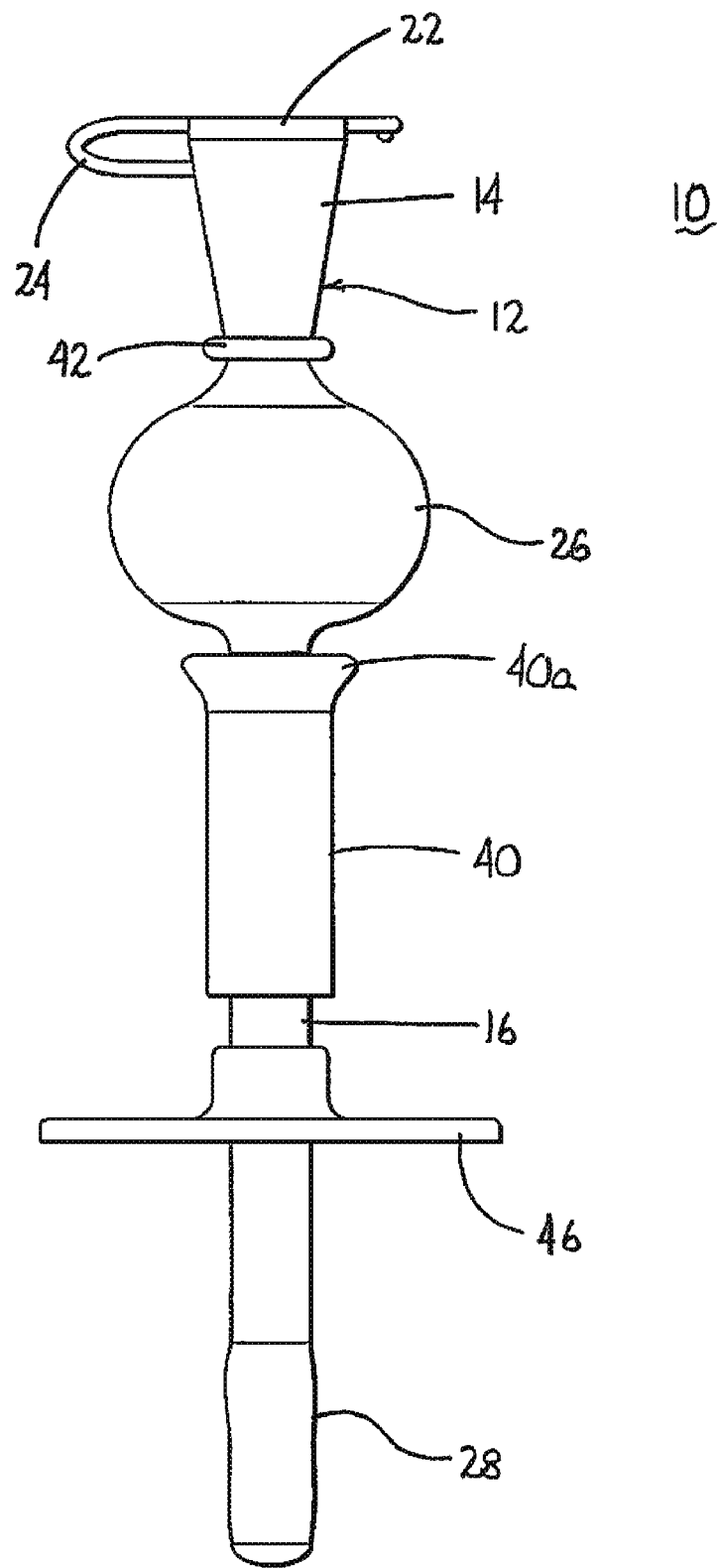
FIG. 1 is a side elevation of one embodiment of the presently disclosed medical device having a transfer sleeve spaced from a prefilled balloon.

Embodiments of the presently disclosed medical device will now be described in detail with reference to the drawings wherein like reference numerals designate identical or corresponding elements in each of the several views. In this description, the term "proximal" is generally used to indicate relative nearness of a referenced item to a user of the device and the term "distal" is used to indicate relative remoteness of a referenced item to a user of the device.

FIG. 1 illustrates one embodiment of the presently disclosed medical device designated generally by the reference number 10. Although the medical device 10 is illustrated as a gastrostomy tube, it is envisioned the principles described herein with respect to the medical device are applicable to many different medical devices including urinary catheters and various types of indwelling catheters.

Figure 2:
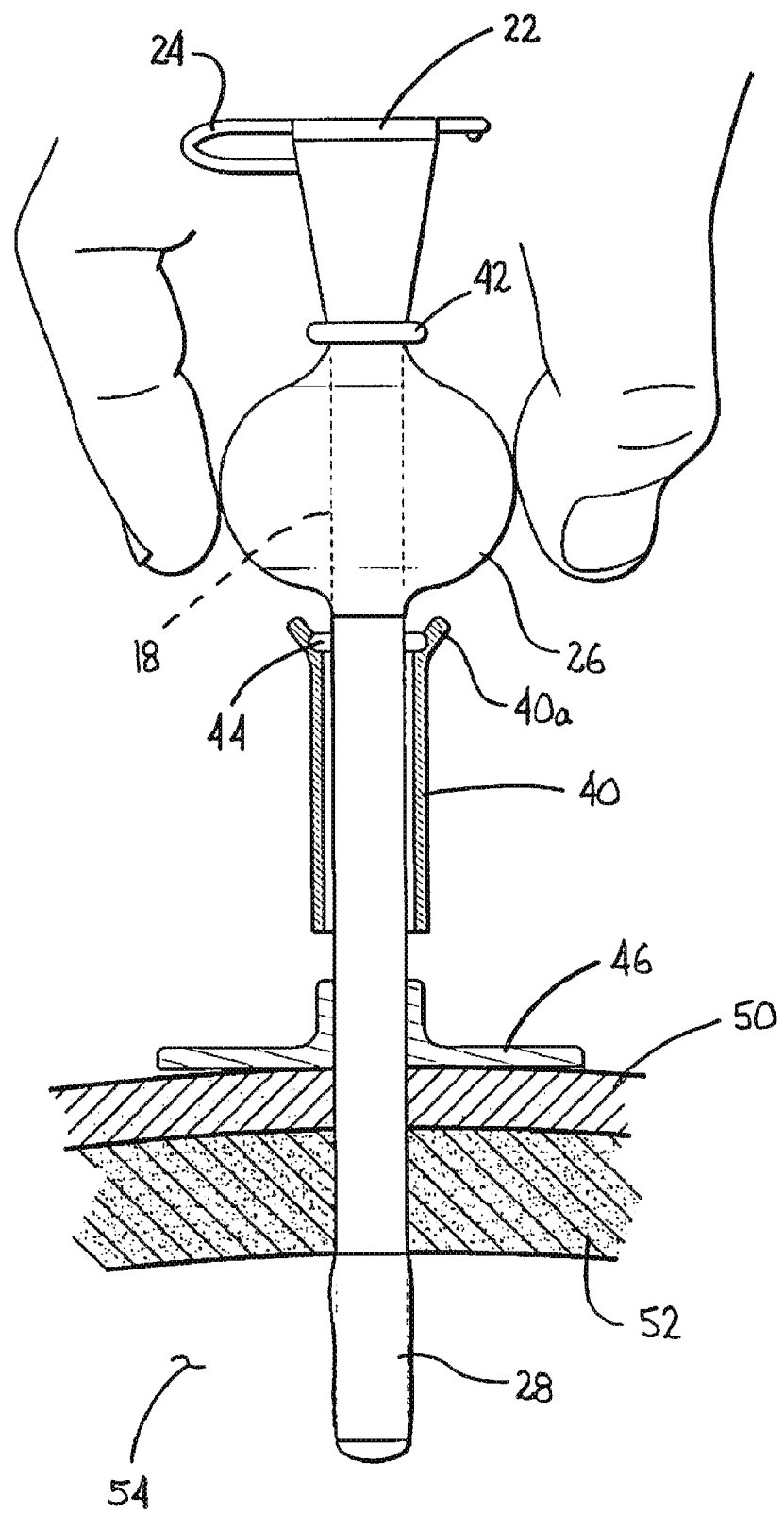
FIG. 2 is a side elevation of the medical device shown in FIG. 1 having its distal end positioned within a body cavity.
Figure 3:
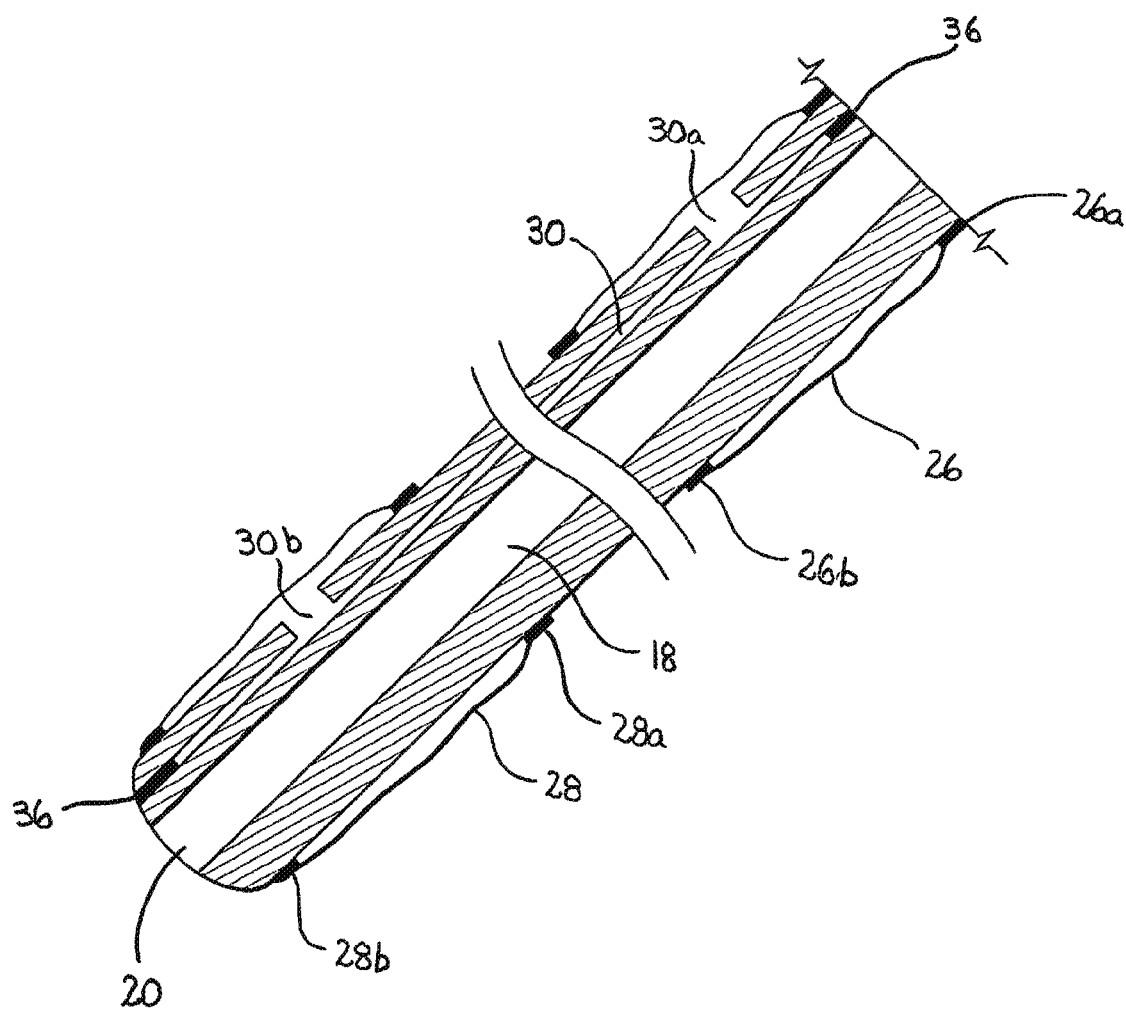
FIG. 3 is a cross-sectional fragmentary detail of an element of the medical device illustrating the prefilled balloon and a securement balloon prior to filling.

Referring to FIGS. 1-3, the medical device 10 includes a main element 12 having a proximal hub portion 14 and an elongate tubular portion 16. Element 12 defines a primary lumen 18 extending through the hub portion 14 and the tubular portion 16. The primary lumen 18 has an inlet end (not shown) extending through the hub portion 14 and an outlet end 20 (FIG. 3) extending through the distal end of the tubular portion 16. A cap 22 is provided to seal the inlet end of the primary lumen 18 when the medical device 10 is not in use. As shown, the cap 22 may be connected to the hub portion 14 by a tether 24.

The medical device 10 also includes a prefilled balloon 26 and a securement balloon 28. The prefilled balloon 26 is secured about a proximal end of the tubular portion 16 of the main element 12 and the securement balloon 28 is secured about a distal end of the tubular portion 16 of element 12. Each of the balloon 26, 28 has a first end 26a, 28a, respectively, secured to the tubular portion 16 and a second end 26b, 28b, respectively, secured to the tubular portion 16. The ends of the balloons 26, 28 can be secured to the tubular portion 16 using any known fastening device or technique, including sonic welding, adhesives, clamps, crimping, etc.

Referring to FIG. 3, the tubular portion 16 of the element 12 defines a secondary lumen 30 fluidly communicating the interior of the prefilled balloon 26 with the interior of the securement balloon 28. The prefilled balloon, the securement balloon, and the secondary lumen define a closed fluid system. As illustrated, the lumen 30 has a first end 30a communicating with the prefilled balloon 26 and a second end 30b communicating with the securement balloon 28. The lumen 30 can be formed in the tubular portion 16 by drilling or molding a channel through element 12 and sealing the ends of the lumen with plugs 36. Alternatively, other techniques may be used to form the lumen 30.

Referring again to FIGS. 1 and 2, the medical device 10 includes a transfer sleeve 40 slidably positioned on the tubular portion 16 of the main element 12. In one embodiment, the transfer sleeve 40 is substantially cylindrical and includes a funnel-shaped upper end 40a. The transfer sleeve 40 is slidable upward on the tubular portion 16 from a first position spaced from the prefilled balloon 26 to a second position located over the prefilled balloon 26. In one embodiment, a base of the hub portion 14 includes an annular rib 42 received in snap-fit fashion in an annular recess 44 formed in upper end 40a of the transfer sleeve 40 to retain the transfer sleeve 40 in its second position. Alternatively, other retaining members or structure may be provided to retain the transfer sleeve 40 in its second position.

The medical device 10 also includes an external anchor such as a skin disk 46 which is fixedly attached around the tubular portion 16 at a location proximal to the securement balloon 28 and distal to the transfer sleeve 40. Skin disk 46 may include a disk-shaped element. Alternatively, other anchor configurations are envisioned. Skin disk 46 is positioned to engage an outer surface of a body of a patient, e.g., an abdominal wall, to maintain the medical device in a tight, wiggle-free relationship with the body of the patient.

Referring to FIG. 2, a fluid is provided in the prefilled balloon 26 such that the prefilled balloon 26 is normally in a distended or inflated state. Each of the balloons 26 and 28 is formed from a resilient or elastomeric material and is stretchable from a deflated state to an inflated state. In one embodiment, the securement balloon 28 is formed from a material or is of a thickness, elasticity, resilience, and/or hardness that the securement balloon 28 is stronger than the prefilled balloon 26. Thus, when fluid is added to the channel 30 (FIG. 3) during manufacturing, the prefilled balloon 26 will move from its deflated state to its inflated state prior to movement of the securement balloon 28 from its deflated state to its inflated state. The volume of fluid added to the closed fluid system defined by the prefilled balloon, the secondary lumen, and the securement balloon when the transfer sleeve 40 is moved to its second position around the prefilled balloon 26, the prescribed amount of fluid will be forced from the prefilled balloon 26 through the channel 30 into the securement balloon 26.

Referring to FIG. 2, after manufacture and during shipping, the transfer sleeve 40 is positioned in its first position, spaced from the prefilled balloon 26, such that the prefilled balloon is in its inflated state and the securement balloon 28 is in its deflated state. By maintaining the securement balloon 28 in its deflated state prior to use, i.e., during shipping and prior to use, the shelf life of the securement balloon 28 is increased.

Figure 4:
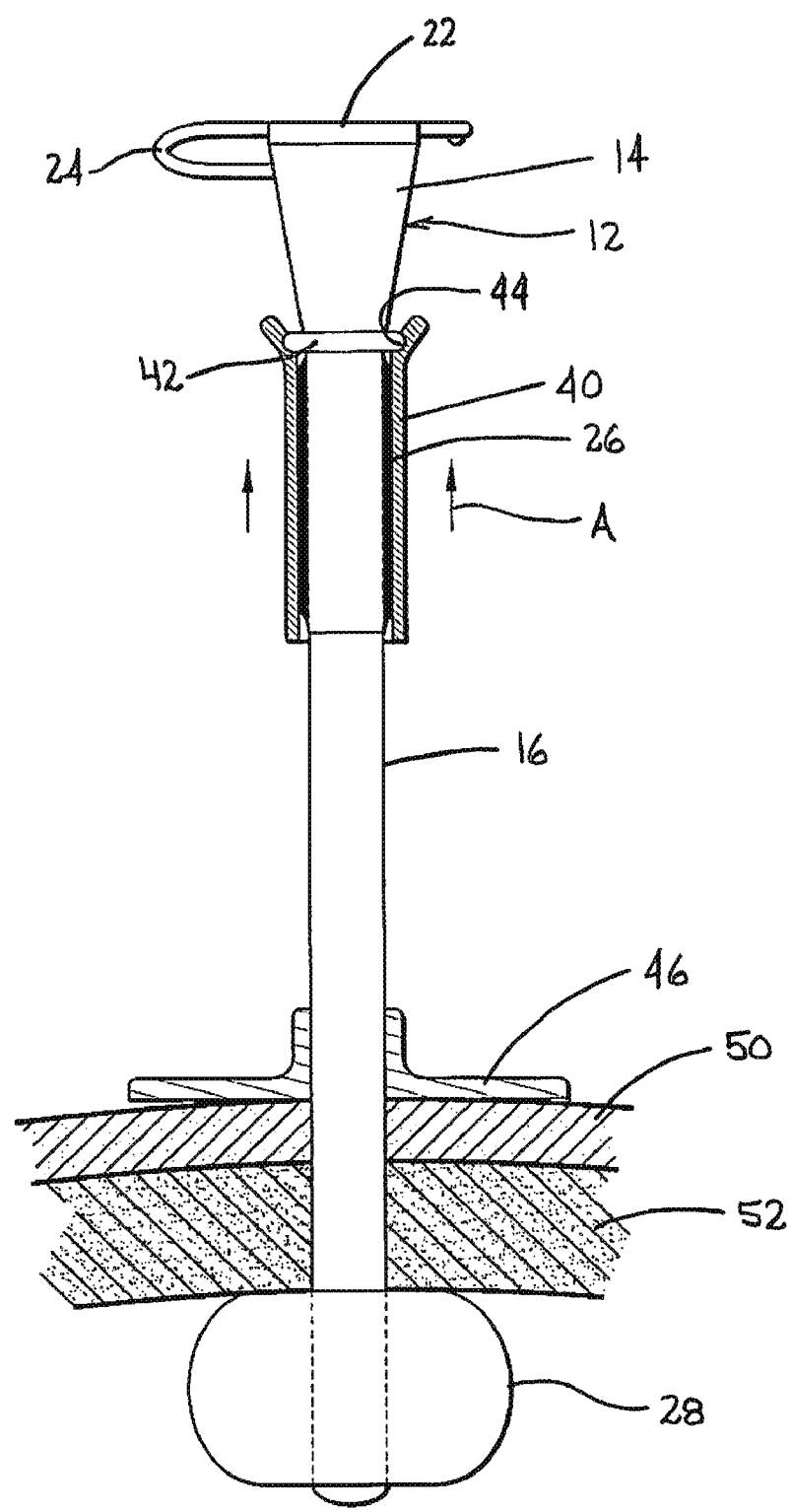
FIG. 4 is a side elevation of the medical device shown in FIG. 2 having the transfer sleeve positioned around the prefilled balloon.

Referring to FIG. 2, in use, the distal end of the tubular portion 16 is inserted through a body incision, e.g., a stoma in an abdominal wall 50 and a stomach wall 52, and into a body cavity, e.g., a stomach 54 of the patient. During insertion, the transfer sleeve 40 is in the first position so the prefilled balloon 26 is substantially inflated, and the securement balloon 28 is substantially deflated. Referring to FIG. 4, after the distal end of the tubular portion 16 is properly positioned in the body cavity, the transfer sleeve 40 is moved upward in the direction indicated by arrow "A" in FIG. 4 to its second position to compress the prefilled balloon 26 and retain the prefilled balloon in a substantially deflated state. As this movement occurs, fluid from the prefilled balloon 26 is forced through the channel 30 (FIG. 3) in the tubular portion 16 of the element 12 into the securement balloon 28 to substantially inflate the securement balloon to a prescribed degree. When the securement balloon 28 is properly inflated, a distal end of the medical device 10 is retained in the body cavity. As shown in FIG. 4, a clamp 44 is positioned to engage an external surface of the abdominal wall to retain the medical device 10 in a tight, wiggle-free position. As will be understood by those skilled in the art, when it is desired to remove the medical device 10 from the body, the transfer sleeve 40 need only be shifted back to its first position spaced from the prefilled balloon 26. When the transfer sleeve 40 is shifted, the greater strength of the securement balloon 28 will force fluid from the securement balloon back into the prefilled balloon 26.

Figure 5:
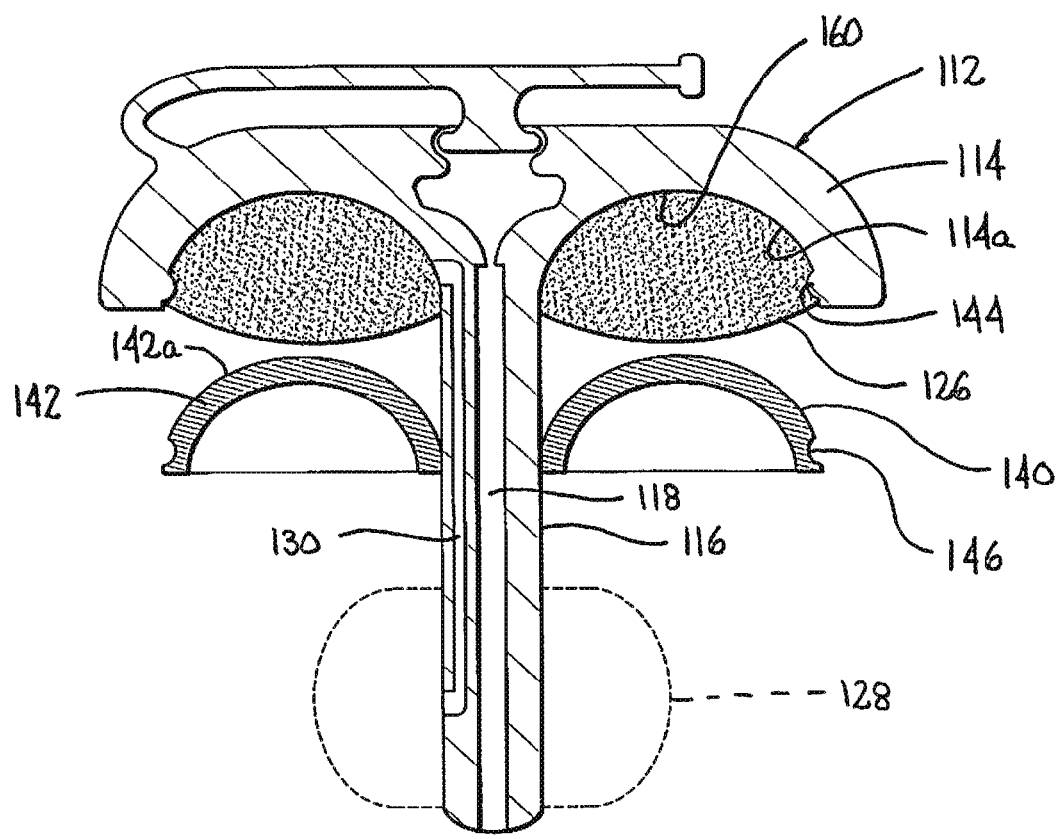
FIG. 5 is a side cross section of an alternative embodiment of the medical device.

FIG. 5 illustrates an alternative embodiment of the presently disclosed medical device 100, also shown as a gastrostomy tube. The medical device 100 operates in a substantially identical manner to the medical device 10 in that the medical device 100 includes a main element 112 having a proximal the hub portion 114 and the tubular portion 116. The element 112 defines a central lumen 118 and a secondary lumen 130. The medical device 100 also includes a prefilled balloon 126, a securement balloon 128 and a transfer sleeve 140. The secondary lumen 130 has a first end communicating with the prefilled balloon 126 and a second end communicating with the securement balloon. The securement balloon 128 has a greater strength than the prefilled balloon 126 such that when fluid is injected into the secondary lumen 130 during manufacturing, the prefilled balloon will inflate prior to inflation of the securement balloon.

The medical device 100 differs from the medical device 10 in that the prefilled balloon 126 is supported in an annular cavity 160 defined by a bottom surface 1 14a of the hub portion 114. In addition, the transfer sleeve 140 has an annular element 142 which is slidably positioned around the tubular portion 116. The annular element 142 includes a convex upper surface 142a dimensioned to be slidably received within the annular concavity 160 of the hub portion 114. A retaining structure including an annular groove or recess 146 is formed on an outer periphery of the upper surface 142a of the transfer sleeve 140. An annular rib 144 is formed around the annular cavity 160 on the bottom surface 114a of the hub portion 114. Similar to the transfer sleeve 40 of the medical device 10, the transfer sleeve 140 is movable from a distal or first position spaced from the prefilled balloon 126 (FIG. 5) to a proximal or second position within the annular cavity 160 to compress the prefilled balloon 126. The annular recess 146 engages the annular rib 140 to releasably lock or retain the transfer sleeve 140 in the second or proximal position. When the prefilled balloon 126 is compressed, fluid within the prefilled balloon is forced to flow through the secondary lumen 130 into the securement balloon 128 to inflate the securement balloon. When the transfer sleeve 140 is returned to its first or distal position, the compressive forces of the securement balloon 128 force fluid from the securement balloon back into the prefilled balloon 126.

Figure 6:
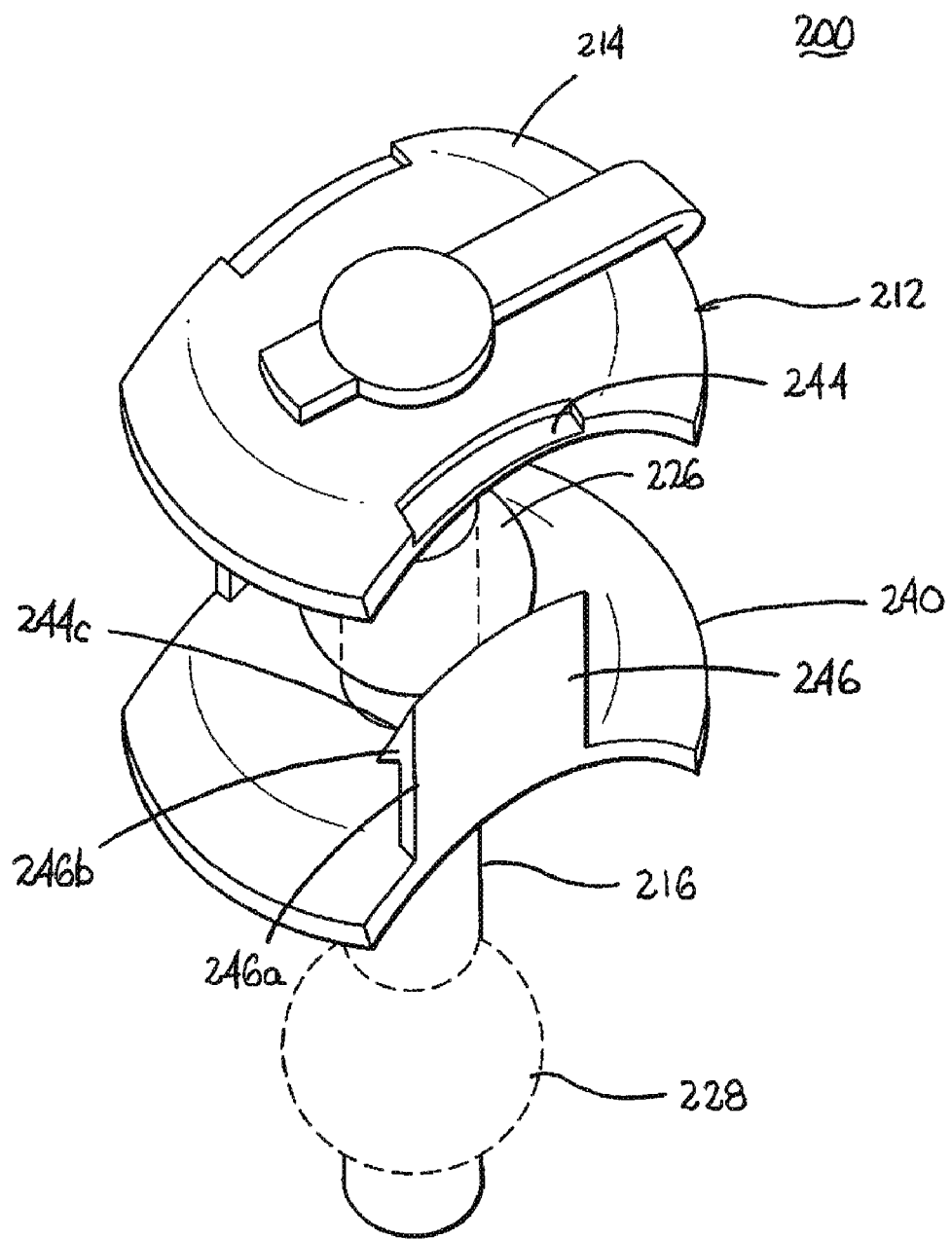
FIG. 6 is a perspective of another alternative embodiment of the medical device.

FIG. 6 illustrates another alternative embodiment of the presently disclosed medical device, generally designated by 200. The medical device 200 operates in a manner similar to the medical device 100 and includes a main element 212 having a hub portion 214 and a tubular portion, a prefilled balloon 226, a securement balloon 228 and a transfer sleeve 240. The medical device 200 differs from the medical device 100 in that the transfer sleeve 240 includes one or more flexible locking arms 246 snap-fit into recesses 244 formed in the hub portion 214 to releasably secure the transfer sleeve 240 in a position located over the prefilled balloon 226. In one embodiment, each locking arm 246 includes a flexible element 246a and a transverse engagement portion 246b. When the transfer sleeve 240 moves from a first position spaced from the prefilled balloon 226 to a second position located over the prefilled balloon 226, a top surface 246c of the engagement portion 246b abuts a bottom surface of the hub portion 214 to deflect the locking tabs 246 outward such that the engagement portions 246b pass the hub portion 214 and snap into the recesses 244 to releasably secure the transfer sleeve 240 in its second position. Alternatively, it is envisioned that a variety of other configurations may be used to releasably retain the transfer sleeve in a position located around the prefilled balloon.

Figure 7:
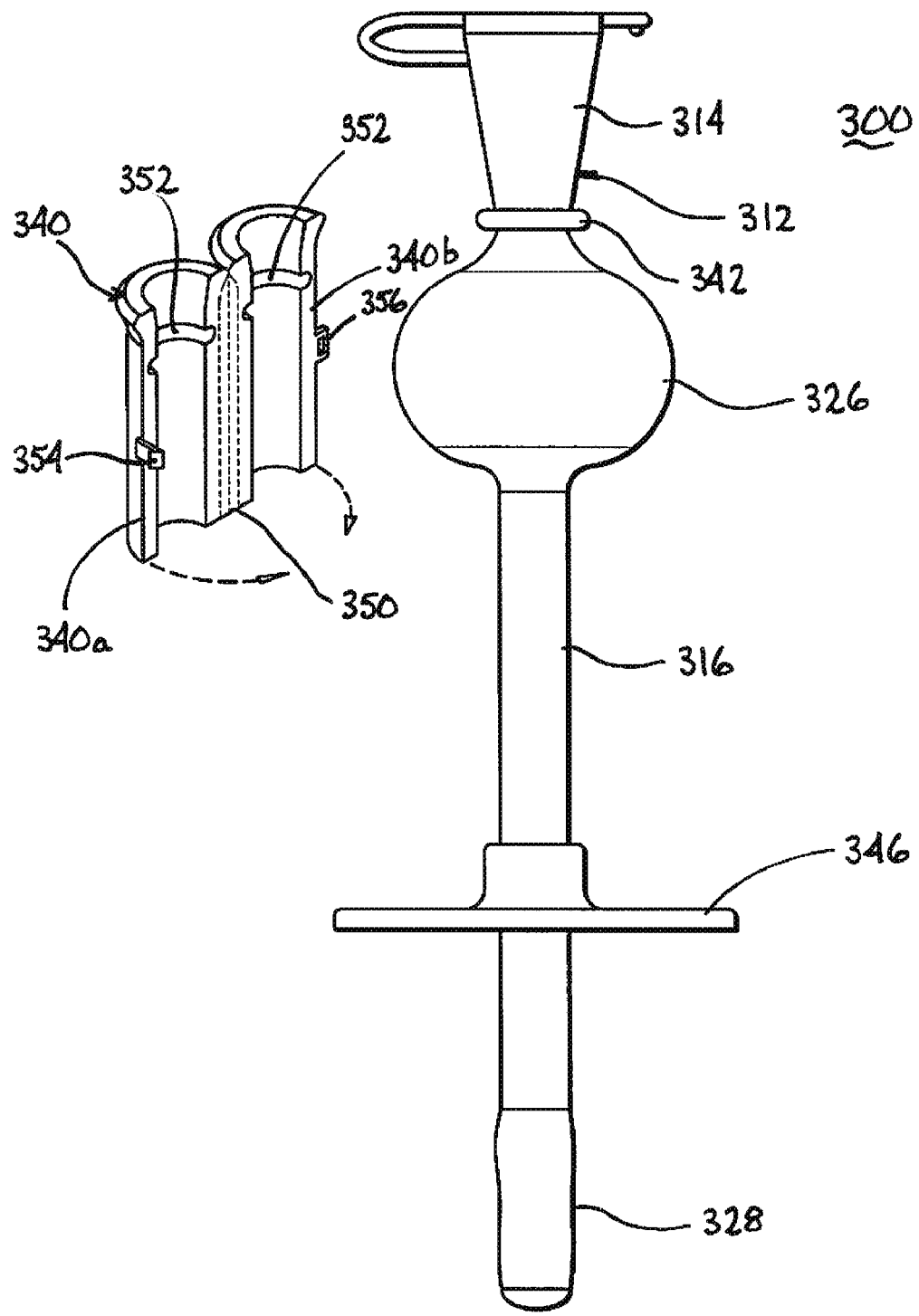
FIG. 7 is a partially separated side elevation of an alternative embodiment of the presently disclosed medical device illustrating its transfer sleeve in perspective.

FIG. 7 illustrates an alternative embodiment of the presently disclosed medical device designated generally by 300. The medical device 300 is substantially similar to the medical device 10 and includes a main element 312 having a proximal hub portion 314 and an elongate tubular portion 316, a prefilled balloon 326, a securement balloon 328 and an anchor such as a skin disk 346. The medical device 300 differs from the medical device 10 in that the transfer sleeve 340 is in the form of a pivotal clam shell. More specifically, the transfer sleeve 340 includes a pair of substantially cylindrical half-sections 340a and 340b pivotally secured together by a hinge member 350. The hinge member 350 may be configured as a living hinge such that the hinge member is integrally formed as half-sections 340a and 340b. Alternatively, the hinge member 350 may be configured as an elongate rod (not shown). Half-sections 340a, 340b are pivotal about the hinge member 350 between an open position shown in FIG. 7 and a closed position (not shown) in which the half-sections 340a, 340b form a substantially cylindrical member dimensioned to be received about the prefilled balloon 326 on the tubular portion 316 of the element 312. The inner portion of each half-section includes a semi-annular recess 352 configured to receive an annular rib 342 formed on a base of the hub portion 314. In the closed position, semi-annular recesses 352 engage the annular rib 342 to axially secure the transfer sleeve 340 around the prefilled balloon 326. Each half-section 340a, 340b includes a latch portion 354, 356, respectively, to secure the half-sections 340a and 340b in the closed position. Latch portions 354, 356 may include snap-fit connectors or the like. Alternatively, other latch configurations are envisioned to secure the half-sections 340a, 340b in the closed position.

In use, after the distal end of the medical device 300 has been inserted into a body cavity, e.g., the stomach, through an opening in the body, e.g., a stoma site, the half-sections 340a, 340b of the transfer sleeve 340 are positioned around the prefilled balloon 326 and moved to the closed position to compress the prefilled balloon 326 and force fluid into the securement balloon 328. Alternatively, a clinician may compress the prefilled balloon 326 with his hands prior to attaching the transfer sleeve 340 around the prefilled balloon. As discussed above, latch portions 354, 356 may be engaged to releasably secure the transfer sleeve 340 around the prefilled balloon 326 in the closed position.

It will be understood that various modifications may be made to the embodiments disclosed herein. Therefore, the above description should not be construed as limiting, but merely as examples of preferred embodiments. Those skilled in the art will envision other modifications within the scope and spirit of the claims appended hereto.

When introducing elements of the present invention or the preferred embodiments(s) thereof, the articles "a", "an", "the", and "said" are intended to mean that there are one or more of the elements. The terms "comprising", "including", and "having" are intended to be inclusive and mean that there may be additional elements other than the listed elements.

What is claimed is:

1. A medical device comprising:
an element having a proximal hub portion and a tubular portion extending distally from the hub portion, the element defining a central lumen extending through the hub portion and the tubular portion, the element also defining a secondary lumen having a first open end and a second open end proximal to the first open end;
a prefilled balloon positioned around the element such that an interior surface of the prefilled balloon operatively communicates with the second open end of the secondary lumen;
a securement balloon positioned around the tubular portion distal to the prefilled balloon such that an interior surface of the securement balloon operatively communicates with the first open end of the secondary lumen, wherein the securement balloon, the secondary lumen, and the prefilled balloon define a closed fluid system having a predetermined volume of fluid and the securement balloon is stronger than the prefilled balloon such that fluid in the closed fluid system is biased toward the prefilled balloon and inflates the prefilled balloon before inflating the securement balloon; and
a transfer sleeve slidably positioned around the tubular portion, the transfer sleeve being movable along the tubular portion from a first position spaced from the prefilled balloon to a second position positioned around the prefilled balloon to urge fluid from the prefilled balloon into the securement balloon to inflate the securement balloon, wherein when the transfer sleeve is in the first position the medical device is in a first condition in which the securement balloon is substantially collapsed and when the transfer sleeve is in the second position the medical device is in a second condition in which the securement balloon is inflated.

2. A medical device according to claim 1 further comprising an anchor supported on the tubular portion proximal to the securement balloon.

3. A medical device according to claim 2 wherein the anchor comprises a skin disk.

4. A medical device according to claim 1 wherein the prefilled balloon is supported around the proximal end of the tubular portion.

5. A medical device according to claim 4 wherein the transfer sleeve is cylindrical and slidably positioned around the tubular portion.

6. A medical device according to claim 5 further comprising retaining structure on the element and the transfer sleeve to releasably retain the transfer sleeve in the second position.

7. A medical device according to claim 6 wherein the retaining structure includes snap-fit connectors.

8. A medical device according to claim 6 wherein the retaining structure includes an annular recess formed on the transfer sleeve and an annular rib formed on the element.

9. A medical device according to claim 1 wherein one end of the transfer sleeve is funnel-shaped.

10. A medical device according to claim 1 wherein the prefilled balloon is supported on a bottom surface of the hub portion of the element.

11. A medical device according to claim 10 wherein the bottom surface of the hub portion defines a concave annular recess.

12. A medical device according to claim 11 wherein the transfer sleeve is slidably positioned around the tubular portion and configured to be received within the concave annular recess of the hub portion.

13. A medical device according to claim 12 further including retaining structure positioned to releasably retain the transfer sleeve in its second position.

14. A medical device according to claim 13 wherein the retaining structure includes an annular groove on the transfer sleeve and an annular rib on the hub portion.

15. A medical device according to claim 13 wherein the retaining structure includes a flexible arm on the transfer sleeve and a recess on the hub portion.

16. A medical device comprising:
an element having a proximal hub portion and a tubular portion extending distally from the hub portion, the element defining a central lumen extending through the hub portion and the tubular portion, the element also defining a secondary lumen having a first open end adjacent a distal end of the element and a second open end adjacent a proximal end of the element;
a prefilled balloon positioned around the proximal end of the element such that an interior surface of the prefilled balloon communicates with the second open end of the secondary lumen;
a securement balloon positioned about the distal end of the tubular portion such that an interior surface of the securement balloon communicates with the first open end of the secondary lumen, the securement balloon, the secondary lumen, and the prefilled balloon define a closed fluid system having a predetermined volume of fluid and the securement balloon is stronger than the prefilled balloon such that fluid in the closed fluid system is biased toward the prefilled balloon and inflates the prefilled balloon before inflating of the securement balloon; and
a transfer sleeve positionable around the prefilled balloon to urge fluid from the prefilled balloon into the securement balloon to inflate the securement balloon.

17. A medical device according to claim 16 wherein the transfer sleeve includes a pair of semi-cylindrical half-sections.

18. A medical device according to claim 17 wherein:
the half-sections are pivotally attached to each other, the half-sections being pivotal from an open position to a closed position; and
in the closed position, the half-sections define a cylindrical member sized to be received around the prefilled balloon.

19. A medical device according to claim 18 wherein the transfer sleeve includes latch portions configured to retain the transfer sleeve in the closed position.

20. A medical device according to claim 17 wherein the semi cylindrical half-sections are joined by a living hinge.

* * * * *